United States Patent
Pourmand et al.

(10) Patent No.: US 7,238,486 B2
(45) Date of Patent: Jul. 3, 2007

(54) DNA FINGERPRINTING USING A BRANCH MIGRATION ASSAY

(75) Inventors: Nader Pourmand, Mountain View, CA (US); Ronald W. Davis, Palo Alto, CA (US); Shan X. Wang, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 63 days.

(21) Appl. No.: 11/231,657

(22) Filed: Sep. 20, 2005

(65) Prior Publication Data
US 2007/0065835 A1    Mar. 22, 2007

Related U.S. Application Data

(60) Provisional application No. 60/612,000, filed on Sep. 21, 2004.

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS

| | | | |
|---|---|---|---|
| 4,725,537 A | 2/1988 | Fritsch et al. ............ | 435/6 |
| 4,766,062 A * | 8/1988 | Diamond et al. ......... | 435/6 |
| 5,753,439 A | 5/1998 | Smith et al. ............. | 435/6 |
| 6,090,549 A * | 7/2000 | Mirzabekov et al. ..... | 435/6 |
| 6,150,095 A | 11/2000 | Southern et al. ......... | 435/6 |
| 6,238,927 B1 | 5/2001 | Abrams et al. .......... | 436/94 |
| 6,261,784 B1 | 7/2001 | Nadeau et al. ........... | 435/6 |
| 6,379,888 B1 | 4/2002 | Nadeau et al. ........... | 435/6 |
| 6,579,680 B2 | 6/2003 | Frutos et al. ............ | 435/6 |
| 6,815,164 B2 | 11/2004 | Kurn ...................... | 435/6 |
| 2004/0235004 A1 | 11/2004 | Yang et al. .............. | 435/6 |

OTHER PUBLICATIONS

R. Radtkey et al., in "Rapid, high fidelity analysis of simple sequence repeats on an electronically active DNA chip" Nucleic Acids Research, 28:E17 (2000).

* cited by examiner

Primary Examiner—Ethan Whisenant
(74) Attorney, Agent, or Firm—Lumen Intellectual Property Services, Inc.

(57) ABSTRACT

A method of determining the length of a polynucleotide target is provided. With this method, a target is first hybridized to an array of first probes having different, determined lengths, resulting in the formation of duplexes between the polynucleotide target and the first probes. These duplexes have a single stranded section of target if the target is longer than the first probe it is in a duplex with. Next, a second probe having a determined length is hybridized to these duplexes. If the length of the target is greater than the length of the first probe it is displaced during this hybridization step by the process of branch migration. In contrast, if the length of the target is less than or equal to the length of the first probe, it is not displaced. Thus, the length of the polynucleotide target can be determined.

10 Claims, 2 Drawing Sheets
(1 of 2 Drawing Sheet(s) Filed in Color)

DNA FINGERPRINTING USING A BRANCH MIGRATION ASSAY

CROSS-REFERENCE TO RELATED APPLICATIONS

This application claims priority from U.S. Provisional Application No. 60/612,000, filed Sep. 21, 2004, which is incorporated herein by reference.

STATEMENT REGARDING FEDERALLY SPONSORED RESEARCH OR DEVELOPMENT

This invention was made in part with government support under grant no. NOOO14-02-0807 awarded by the U.S. Defense Advanced Research Projects Agency. The government has certain rights in this invention.

FIELD OF THE INVENTION

The present invention relates generally to DNA fingerprinting. More particularly, the present invention relates to a method of determining the length of a polynucleotide target using a branch migration assay.

BACKGROUND

DNA fingerprinting (also known as DNA profiling) using short tandem repeats (STRs) has become the method of choice for human identification in forensic sciences, finding applications in different circumstances such as determination of perpetrators of violent crime, resolving unestablished paternity, and identifying remains of missing persons or victims of mass disaster. STRs are highly polymorphic microsatellite regions of 2–7 bp localized in noncoding regions of DNA. Every individual has a different pattern of STRs due to a different number of repeats and microvariation in the sequences of the repeats.

The FBI and the forensic science community typically use 13 separate STR loci (the core CODIS loci) in routine forensic analysis. (CODIS refers to the Combined DNA Index System that was established by the FBI in 1998). If two DNA samples have identical lengths at all 13 loci, the probability that the two samples did not originate from the same individual is approximately one to ten billion. The courts generally accept this identification as definitive evidence that the individuals in question are the same. It is believed that STR analysis will remain the technique of choice in forensic science for DNA fingerprinting for the next decade, and that the number of loci used in this analysis will perhaps increase from 13 to 20.

Generally, to perform a DNA fingerprinting experiment based on STR analysis, the regions of DNA corresponding to each of the 13 STR loci are excised from sample DNA using appropriate restriction enzymes. The regions are then amplified using PCR and labeled with a dye or fluorescent molecule. The length of the DNA molecules is then determined using polyacrylamide gel electrophoresis (PAGE) or other known electrophoretic separation techniques, see, e.g., John M. Butler "Forensic DNA Typing" Academic Press, 2001.

Electrophoresis is a separation technique based on size, i.e., shorter DNA molecules migrate more rapidly down a gel or capillary than longer DNA molecules. The population of molecules (in this case, STR regions) is thus separated by size (or repeat length), and the final position of the DNA is determined by visualizing the staining pattern of the dye or fluorescent molecule. While there are miniature systems with an array of electrophoretic columns for this measurement, the number of STR regions and samples that can be identified using these miniature systems is relatively small.

Although still in their infancy, several DNA fingerprinting methods using microarrays have been proposed. For example, R. Radtkey et al., in "Rapid, high fidelity analysis of simple sequence repeats on an electronically active DNA chip" *Nucleic Acids Research,* 28:E17 (2000), offer a high stringency approach for discriminating STR alleles based on active microarray hybridization. A sandwich hybrid is assembled, in which proper base stacking of juxtaposed terminal nucleotides results in a thermodynamically favored complex. The increased stability of this complex relative to non-stacked termini and/or base pair mismatches is used to determine the identification of STR alleles. While this method has the advantage of being able to test many samples and STRs in a small instrument, it has the disadvantage of requiring the use of a special electronically active DNA array to allow discrimination of subtle hybridization differences between repeats of similar lengths. Thus, this method has not been widely adopted.

Another proposed microarray method involves the use of ligase and/or polymerase to detect the length of a VNTR (variable number of tandem repeats). For example. U.S. Pat. No. 6,150,095 discloses a technique in which the length of a VNTR is detected by hybridizing a target to a short probe to form a duplex, incubating the duplex with labeled nucleotides, and monitoring chain extension of the probe as an indication of the length of the variable number repeat section of the target. Other methods to determine the length of VNTR involve the use of ligation of tags combined with base extension. VNTR-based DNA fingerprinting has largely been superseded by STR-based DNA fingerprinting.

U.S. Pat. No. 5,753,439 discloses a method of using nuclease to nick mismatched base pairs followed by nick translation using DNA polymerase. With this method, target DNA is labeled and hybridized to a differently labeled probe. Mismatched bases due to differences in the length of the repeat region between the probe and the target are nicked with nuclease, and the remainder of the probe or target is elongated using nick translation, thereby displacing the label on the target or probe. This method is complicated and thus has not gained wide adoption.

Accordingly, there is a need in the art to develop new, simple DNA fingerprinting methods utilizing widely available microarrays for rapid determination of individual identity.

SUMMARY OF THE INVENTION

The present invention provides a method of determining the length of a polynucleotide target that takes advantage of the process of branch migration. Branch migration is a process by which a single invading single-stranded polynucleotide extends its partial pairing with its complimentary strand as it displaces the resident strand from a polynucleotide duplex. With this method, a polynucleotide target is first hybridized to an array of first probes having different, determined lengths, resulting in the formation of duplexes between the polynucleotide target and the first probes. These duplexes have a single stranded section of target polynucleotide if the target polynucleotide is longer than the first probe it is in a duplex with. Next, a second probe having a determined length is hybridized to these duplexes. Preferably, the second probe is similar in sequence to the sequence of one of the immobilized probes. More preferably, is identical in sequence to one of the first probes. Alternatively, the second probe may be an array of probes that are identical to the array of first probes. If the length of the target polynucleotide is greater than the length of the first probe, and thus has a single stranded section, it is displaced during this hybridization step by the process of branch migration. In contrast, if the length of the target polynucleotide is less than or equal to the length of the first probe, it is not displaced.

Thus, the length of the target polynucleotide can be determined by identifying in which duplexes the target polynucleotide was displaced.

The target polynucleotide and first and second probes may be any nucleic acid or nucleic acid analog, preferably single or double-stranded DNA. In the case of double-stranded DNA, the DNA is denatured prior to hybridization, e.g. by heating to 95° C. Preferably, the target polynucleotide and first and second probes have repeated nucleotide sequences, with the number of repeated sequences in the target polynucleotide and first and second probes determining the lengths of the target polynucleotide and first and second probes. The repeated sequences may be of any length, but are preferably between about 2 to about 7 base pairs long. Examples of repeated sequences identifiable by this invention include short tandem repeats (STRs) and trinucleotide repeats. In a preferred embodiment, the first and second probes also have a non-repeated nucleotide sequence that is complimentary to a non-repeated nucleotide sequence in the target.

In a preferred embodiment, only the target polynucleotide is labeled. Alternatively, the target polynucleotide, first and second probes may be labeled with distinct labels, respectively. Any label may be used, including but not limited to fluorescent particles, magnetic nanoparticles, and biotin.

Preferably, the array of first probes is attached to a solid support. More preferably, the first probes are attached to predetermined positions on the solid support to form a microarray. The array of first probes may be attached by any means, including but not limited to chemical linkage, biological linkage, sulfur linkage of probes modified with a sulfur containing group, and amino-linkage of probes modified with an amine group.

BRIEF DESCRIPTION OF THE FIGURES

The patent or application file contains at least one drawing executed in color. Copies of this patent or patent application publication with color drawing(s) will be provided by the Office upon request and payment of the necessary fee.

The present invention together with its objectives and advantages will be understood by reading the following description in conjunction with the drawings, in which.

DETAILED DESCRIPTION OF THE INVENTION

Figure 1:
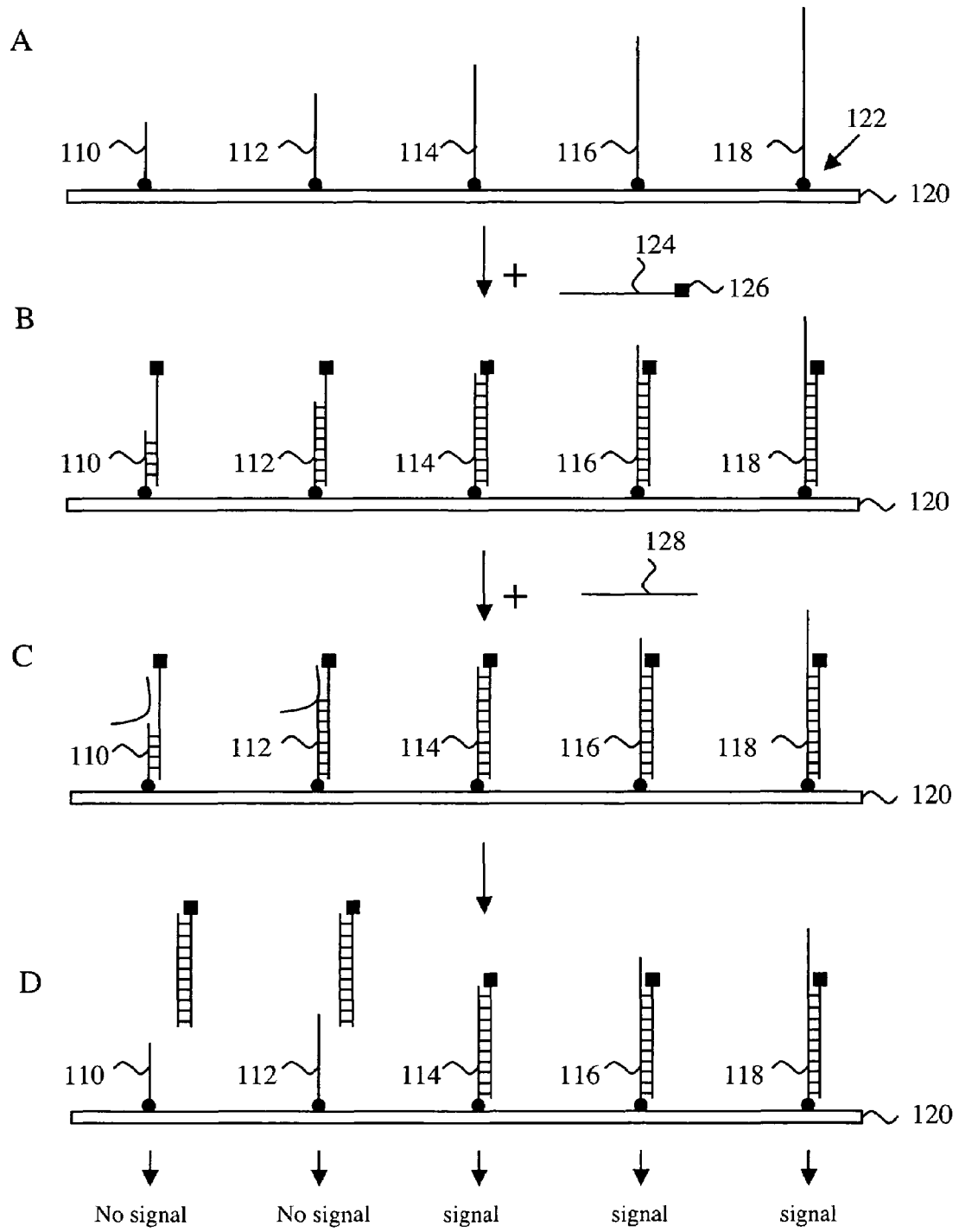
FIG. 1 shows an example of a branch migration assay according to the present invention.

The present invention provides a method of determining the length of a polynucleotide target using a branch migration assay, an example of which is shown in FIG. 1. In this example, an array of single-stranded polynucleotide first probes 110, 112, 114, 116, 118, having one, two, three, four, and five repeats, respectively, are attached to the surface of microarray 120 through attachment domain 122 (FIG. 1A). In a first step, a single-stranded target polynucleotide 124 labeled with label 126 and having three repeats is hybridized to the first probes (FIG. 1B). Target polynucleotide 124 hybridizes with first probes 110 and 112 to form a duplex with a single-stranded region of target polynucleotide 124. The duplex formed by target polynucleotide 124 and first probe 114 has no single-stranded regions. The duplex formed by target polynucleotide 124 and first probes 116 and 118 has single-stranded regions of first probe.

Next, an unlabeled single-stranded polynucleotide second probe 128, which is complimentary to target polynucleotide 124, is hybridized with the duplexes (FIG. 1C). Branch migration is more thermodynamically favorable in the presence of single-stranded polynucleotide. Thus, second probe 128 displaces target polynucleotide 124 only from the duplexes in which there is a single stranded region of target polynucleotide 124 present, i.e. the duplexes containing probes 110 and 112 (FIG. 1D). Displacement of target polynucleotide 124 from probes 110 and 112 can be detected by a loss of signal due to displacement of label 126 from these duplexes. By identifying which duplexes have had target polynucleotide 124 displaced, the length, and hence the number of repeats, in target polynucleotide 124 can be determined. In this case, since signal is lost from duplexes containing first probes 110 and 112, having one and two repeats, respectively, target polynucleotide 124 is determined to have three repeats.

A key requirement for this assay is that the target polynucleotide hybridizes to the first probes in the proper register. That is, it must hybridize without misaligned repeats or "slippage".

For example, in FIG. 1B, it must be ensured that polynucleotide target 124 binds probes 116 and 118 starting at the repeat on the first probe that is closest to the microarray surface.

Otherwise, the polynucleotide target could hybridize to first probes 116 and 118 such that there is a single stranded region of polynucleotide target in addition to a single-stranded region of probe in the duplex. This would result in displacement of the polynucleotide target from probes 116 and 118 by second probe 128, loss of signal 126 from probes 116 and 118, and misidentification of the number of repeats in polynucleotide target 124. Therefore, in a preferred embodiment, the first and second probes contain a non-repeated nucleotide sequence that is complementary to a non-repeated sequence on the polynucleotide target. For example, if the first probe is attached to the surface of the microarray at the 5' end, there would be a non-repeated sequence 5' to the repeated sequences in the first probe, which is complimentary to the target polynucleotide. The same sequence would be present in the 5' end of the second probe.

The branch migration assay may be carried out with any detection system, for instance, a standard fluorescence technology. In addition to conventional fluorescence microarrays, the assay could also be carried out using high-sensitivity magnetic detector arrays such as spin-valve arrays and magnetic tunneling junction arrays.

EXAMPLE

First Probe Preparation

The first probes were prepared by oligonucleotide synthesis. Probes were synthesized for detection of 7 STR loci (TPOX, CSF1PO, D5S818, D7S820, D13S317, D16S539, D18S51) each having from 1 to 16 repeats. These STR loci are the simplest ones, with just 4 nucleotides repeated and no variation in sequence. The first probes were synthesized with an amino-modification at the 5' end that allows the oligo to bind to the chip surface, followed by a common sequence, a unique sequence (a genomic sequence located 3' of the repeats, which is specific for each STR locus) and nucleotide repeats (from 1 to 16), so that for each STR locus there were 16 probes. The unique sequence and the repeats were both complementary to the genomic sequence of the target. Table 1 shows the sequences of the first probes (SEQ ID NO: 1–7), with the amino modification shown between slashes, the common sequence shown in plain text, the unique sequence underlined, and the repeat sequence in bold. Only one repeat is shown for each STR probe in Table 1.

TABLE 1

| STR name | SEQ ID NO: | SEQUENCE |
|---|---|---|
| TPOX | 1 | 5'-/5AmMC6/TTCTGAGCCACTTGGACTGAG<u>AGCGTTTATTTGCCC</u>AAACATT |
| CSF1PO | 2 | 5'-/5AmMC6/TTCTGAGCCACTTGGACTGAG<u>CTGTTCTAAGTACTTCCT</u>ATCT |
| D5S818 | 3 | 5'-/5AmMC6/TTCTGAGCCACTTGGACTGAG<u>TTATACCTCTATCTACCT</u>ATCT |
| D7S820 | 4 | 5'-/5AmMC6/TTCTGAGCCACTTGGACTGAG<u>AAAAACTATCAATCTGTC</u>TATC |
| D13S317 | 5 | 5'-/5AmMC6/TTCTGAGCCACTTGGACTGAG<u>AAAGATAGATAGATGATT</u>GATA |
| D16S539 | 6 | 5'-/5AmMC6/TTCTGAGCCACTTGGACTGAG<u>TGTTTTGTCTTTCAATGA</u>TATC |
| D18S51 | 7 | 5'-/5AmMC6/TTCTGAGCCACTTGGACTGAG<u>CCCTCTCTTTTTCTTACT</u>TTCT |

Microarray Printing

The chips used for the printing were CodeLink Activated Slides (Amersham Biosciences) that covalently immobilize amine-modified DNA. The printing mix was: 20 µM amine-modified first probe DNA, 60 µM DNA spacer (PolyT), and IX printing buffer (50 mM sodium phosphate, pH 8.5). The printing was performed with an OmniGrid™ printer (GeneMachines™). Each probe sample was printed 4 times per array and 2 arrays were present in each chip. The slides were left overnight in a humid chamber and the day after were blocked with 0.1 M Tris, 50 mM ethanolamine at pH 9.

First Hybridization

The first hybridization was performed first with target oligonucleotides (oligos) having a known sequence; different STR loci and different numbers of repeats were tested. The target oligos had the unique sequence described above at the 3' end, repeats and a universal sequence (non-genomic sequence, the same for all the STR loci) at the 5' end. To obtain these target oligos two PCR reactions were conducted on plasmids containing repeat regions, a unique sequence for each STR locus and a universal region. The first PCR reaction used unique and universal primers. The second PCR reaction used only biotinylated universal primer in order to obtain labeled single stranded DNA. After PCR purification with QIAquick PCR Purification Kit (Qiagen), hybridization was performed overnight at 50° C. in the presence of 30 µl PCR product, 2× hybridization buffer (100 mM MES, IM [Na+], 20 mM EDTA, 0.01% Tween20), 1.25× Denhardt's solution and 1 µl of a fluorescently labeled universal oligo with phycoerythrin (which was complementary to the common sequence present in all of the printed oligos).

Second Hybridization

After washing the chip twice in SSPE 6× and Tween 0.1% at 50° C. for 1 min and once in SSPE 6× and Tween 0.1% at room temperature for 1 min, a second hybridization (branch migration) was conducted with one of the amino-oligos used for the printing that had a higher number of repeats than the target oligo. This hybridization was conducted with 7.5 pmol/µl of oligo (250 times more concentrated than what was used in the printing mix), 10 mM MgCl$_2$ and 4×SSC for 4 hours at 50° C. The chips were then washed twice in SSPE 6× and Tween 0.1% at 50° C. for 1 min and once in SSPE 6× and Tween 0.1% at room temperature for 1 min. Next, the chip was labeled with 0.0017 µg/µl streptavidin-allophycocyanin conjugate, 6×SSPE, 1× Denhardt's solution and 0.01% Tween 20 for 10 min at 50° C. The chip was then washed twice in SSPE 6× and Tween 0.1% at 50° C. for 1 min and once in SSPE 6× and Tween 0.1% at room temperature for 1 min.

Human Genomic DNA Samples

In another experiment (not shown) human genomic DNA was used as the target. In this case, the target polynucleotides were prepared by conducting a first PCR reaction with a forward primer having a unique sequence complimentary to a genomic sequence at the 3' end of the repeats and a reverse primer having a unique sequence complimentary to a genomic sequence at the 5' end of the repeats. A second PCR reaction was conducted using only biotinylated forward primer in order to obtain labeled single-stranded DNA. For the second hybridization (branch migration), both the protocol described above under second hybridization, and a protocol using 100 mM MgCl$_2$ and hybridization overnight at 50° C. were tested. Results from this experiment enabled determination of repeat number.

Results

Figure 2:
FIG. 2 shows an example of results from a branch migration assay according to the present invention.

FIG. 2 shows images of a chip before hybridization (FIG. 2A), after the first hybridization (FIGS. 2B and C) and after the second hybridization, i.e. branch migration (FIG. 2D). In FIG. 2A, the green spots show where the first probes were printed, in this case probes that detect STR DS18S51 with from 1 to 16 repeats (labeled as D18-1 to D18-16). There were four first probes printed for each STR repeat number, shown by the four green spots corresponding to each labeled first probe. In FIG. 2B, the red spots demonstrate binding of biotinylated target (red) to an unlabeled probe. In FIG. 2C, the yellow spots show where there are both first labeled probes printed (green) and biotinylated target (red) hybridized to the first probes. As can be seen from FIG. 2C, the first hybridization conditions successfully allow target to hybridize to all the first probes. FIG. 2D shows an image of a chip that was first hybridized with a biotinylated target oligo containing 3 repeats, and was then hybridized with a second probe containing 5 repeats. The image shows that the target oligo was displaced from the eight spots corresponding to first probes having 1 and 2 repeats (i.e. there is only green label on these spots, corresponding to the presence of first probes). In contrast, the target oligo remained hybridized to the spots corresponding to first probes having from 3 to 16 repeats (i.e. there is yellow label on these spots, corresponding to the presence of both first probe and biotinylated target). Thus, the number of repeats in the target oligo can be determined to be 3.

Although the present invention and its advantages have been described in detail, it should be understood that the present invention is not limited by what is shown or described herein. As one of ordinary skill in the art will appreciate, the DNA fingerprinting methods disclosed herein could vary or be otherwise modified without departing from the principles of the present invention. Accordingly, the scope of the present invention should be determined by the following claims and their legal equivalents.

What is claimed is:

1. A method of determining the length of a polynucleotide target, comprising:
   (a) hybridizing said polynucleotide target to an array of first probes having different, determined lengths to form duplexes between said polynucleotide target and said first probes;
   (b) hybridizing a second probe having a determined length to said duplexes, wherein said second probe displaces said polynucleotide target from said duplex if the length of said polynucleotide target is greater than the length of said first probe; and
   (c) determining the length of said polynucleotide target by identifying in which of said duplexes said polynucleotide target was displaced.

2. The method as set forth in claim 1, wherein said polynucleotide target, said first probes, and said second probe comprise single-stranded DNA, double-stranded DNA, or nucleic acid analogs.

3. The method as set forth in claim 1, wherein said polynucleotide target, said first probes, and said second probe comprise repeated nucleotide sequences, and wherein the length of said polynucleotide target, said first probes, and said second probes is determined by the number of said repeated nucleotide sequences.

4. The method as set forth in claim 3, wherein said repeated nucleotide sequences comprise two to seven base pairs.

5. The method as set forth in claim 3, wherein said first probes and said second probe further comprise a non-repeated nucleotide sequence that is complimentary to a non-repeated nucleotide sequence in said target.

6. The method as set forth in claim 1, wherein said second probe has a nucleotide or nucleotide analog sequence that is identical to the nucleotide or nucleotide analog sequence of one of said first probes.

7. The method as set forth in claim 1, further comprising labeling said polynucleotide target and said first probes.

8. The method as set forth in claim 7, wherein said label comprises biotin, fluorescent particles, or magnetic nanoparticles.

9. The method as set forth in claim 1, further comprising attaching said array of first probes to a solid support.

10. The method as set forth in claim 9, wherein said first probes are attached to predetermined positions on said solid support.

* * * * *

SEQUENCE LISTING

<160> NUMBER OF SEQ ID NOS: 7

<210> SEQ ID NO 1
<211> LENGTH: 43
<212> TYPE: DNA
<213> ORGANISM: Artificial
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: AmMC6

<400> SEQUENCE: 1
ttctgagcca cttggactga gagcgtttat ttgcccaaac att         43

<210> SEQ ID NO 2
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

<400> SEQUENCE: 2
ttctgagcca cttggactga gctgttctaa gtacttccta tct         43

<210> SEQ ID NO 3
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

<400> SEQUENCE: 3
ttctgagcca cttggactga gttatacctc tatctaccta tct         43

<210> SEQ ID NO 4
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

<400> SEQUENCE: 4
ttctgagcca cttggactga gaaaaactat caatctgtct atc         43

<210> SEQ ID NO 5
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

-continued

```
<400> SEQUENCE: 5
ttctgagcca cttggactga gaaagataga tagatgattg ata                           43

<210> SEQ ID NO 6
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

<400> SEQUENCE: 6
ttctgagcca cttggactga gtgttttgtc tttcaatgat atc                           43

<210> SEQ ID NO 7
<211> LENGTH: 43
<212> TYPE: DNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: AmMC6

<400> SEQUENCE: 7
ttctgagcca cttggactga gccctctctt tttcttactt tct                           43
```